(12) United States Patent
Simons

(10) Patent No.: US 11,786,685 B2
(45) Date of Patent: Oct. 17, 2023

(54) ORAL AIRWAY DEVICE

(71) Applicant: Kilburn Anesthesia Products LLC, Wichita, KS (US)

(72) Inventor: Fara E. Simons, Wichita, KS (US)

(73) Assignee: Kilburn Anesthesia Products LLC, Wichita, KS (US)

( * ) Notice: Subject to any disclaimer, the term of this patent is extended or adjusted under 35 U.S.C. 154(b) by 250 days.

(21) Appl. No.: 17/099,216

(22) Filed: Nov. 16, 2020

(65) Prior Publication Data

US 2021/0069440 A1  Mar. 11, 2021

Related U.S. Application Data

(63) Continuation of application No. 15/921,915, filed on Mar. 15, 2018, now Pat. No. 10,835,701.

(60) Provisional application No. 62/490,742, filed on Apr. 27, 2017.

(51) Int. Cl.
*A61M 16/04* (2006.01)
*A61B 1/24* (2006.01)
*A61B 1/00* (2006.01)

(52) U.S. Cl.
CPC .... *A61M 16/0493* (2014.02); *A61M 16/0495* (2014.02); *A61M 16/0497* (2013.01); *A61B 1/00154* (2013.01); *A61B 1/24* (2013.01)

(58) Field of Classification Search
CPC ............ A61M 16/0488; A61M 16/049; A61M 16/0493; A61M 16/0495; A61M 16/0497; A61M 2025/022; A61B 1/00154; A61B 13/00
See application file for complete search history.

(56) References Cited

U.S. PATENT DOCUMENTS

| | | | |
|---|---|---|---|
| 3,398,747 A | | 8/1968 | Raimo |
| 3,568,680 A | | 3/1971 | Raimo |
| 3,576,187 A | | 4/1971 | Oddera |
| 3,926,196 A | | 12/1975 | Bomhorst et al. |
| 4,054,135 A | | 10/1977 | Berman |
| 4,112,936 A | | 9/1978 | Blachly |
| 4,559,940 A | | 12/1985 | McGinnis |
| 5,174,284 A | * | 12/1992 | Jackson ............ A61M 16/0493 128/200.26 |
| 5,533,523 A | | 7/1996 | Bass, Jr. et al. |
| 5,590,643 A | * | 1/1997 | Flam ................. A61M 16/0488 128/207.14 |
| 6,257,238 B1 | | 7/2001 | Meah |
| 6,517,549 B1 | * | 2/2003 | Dennis ............. A61M 16/0493 128/200.26 |

(Continued)

*Primary Examiner* — Joseph D. Boecker
(74) *Attorney, Agent, or Firm* — Young Basile Hanlon & MacFarlane, P.C.

(57) ABSTRACT

In one aspect of the present disclosure, an airway device is disclosed that includes a bite block and a depressor section. The bite block has proximal and distal ends and is configured and dimensioned for positioning between a patient's upper and lower teeth. The depressor section also has proximal and distal ends and extends distally from the bite block. The depressor section includes upper and lower members that are separated by a web as well as a stop. The lower member includes a first portion having a generally linear configuration and a second portion having an arcuate configuration, and the stop depends transversely from the first portion of the lower member.

20 Claims, 7 Drawing Sheets

(56) References Cited

U.S. PATENT DOCUMENTS

| | | |
|---|---|---|
| D536,441 S | 2/2007 | Garren et al. |
| D662,586 S | 6/2012 | Coath |
| 8,684,919 B2 | 4/2014 | Anca et al. |
| 9,132,254 B2 | 9/2015 | Anca et al. |
| D847,350 S | 4/2019 | Eaton |
| 2007/0089754 A1 | 4/2007 | Jones |
| 2010/0030027 A1* | 2/2010 | Bastid ............... A61M 16/0488 600/120 |
| 2010/0132700 A1 | 6/2010 | Filipi et al. |
| 2010/0199998 A1 | 8/2010 | Matioc |
| 2012/0143003 A1* | 6/2012 | Anca ................. A61M 16/0497 600/114 |
| 2012/0240922 A1* | 9/2012 | Denyer ............. A61M 15/0021 128/200.15 |
| 2013/0023797 A1* | 1/2013 | Hanewinkel ......... A61B 5/1121 29/428 |
| 2014/0007868 A1 | 1/2014 | Eaton et al. |
| 2014/0275784 A1* | 9/2014 | Joyce ................ A61M 16/0497 600/114 |
| 2015/0265792 A1* | 9/2015 | Goudra .............. A61B 1/00082 600/114 |
| 2016/0256652 A1* | 9/2016 | Wiesman ................ A61B 5/082 |
| 2017/0203067 A1 | 7/2017 | Eaton et al. |
| 2020/0261677 A1* | 8/2020 | Bezerra ............. A61M 16/0495 |

\* cited by examiner

ORAL AIRWAY DEVICE

CROSS-REFERENCE TO RELATED APPLICATIONS

This application is a continuation of U.S. patent application Ser. No.: 15/921,915, filed on Mar. 15, 2018, which claims the benefit of, and priority to, U.S. Provisional Patent Application Ser. No. 62/490,742, filed on Apr. 27, 2017, the entire contents of which are incorporated herein by reference.

BACKGROUND

During certain medical procedures, it is often necessary to insert medical tools, such as endotracheal tubes, e.g., breathing tubes, into a patient's mouth and/or the patient's throat or esophagus. For example, during an esophagogastroduodenoscopy (EGD) procedure, an endoscope is passed through the patient's oral cavity, esophagus, stomach, and duodenum, e.g., for the treatment of abdominal pain, ulcers, cancer, hiatal hernias, GERD (gastrointestinal reflux disease), heartburn, dysphagia (difficulty swallowing), etc. Such medical procedures are often performed while the patient is under general anesthesia (thereby rendering the patient unconscious) or conscious sedation, which creates a potential for the patient's tongue to obstruct or block the patient's airway, thereby complicating the medical procedure.

To combat this issue, the patient's jaw can be lifted, and/or a bypass can be created through the patient's nasal passages. However, lifting the patient's jaw is not always effective, and the insertion of tubes into the nasal passages can sometimes result in bleeding, which is particularly problematic for patients on anti-coagulants and which may cause blood dripping towards the back of the patient's airway to trigger a cough.

As such, there remains a need for a medical device that can not only keep a patient's airway open and clear during medical procedures, but support and protect medical tools inserted into the patient's oral cavity, e.g., from damage by the patient's teeth.

SUMMARY

In one aspect of the present disclosure, an airway device is disclosed that includes a bite block and a depressor section. The bite block has proximal and distal ends and is configured and dimensioned for positioning between a patient's upper and lower teeth. The depressor section also has proximal and distal ends and extends distally from the bite block. The depressor section includes upper and lower members that are separated by a web, as well as a stop. The lower member includes a first portion having a generally linear configuration and a second portion having an arcuate configuration, and the stop depends transversely from the first portion of the lower member.

In certain embodiments, the stop may be positioned in generally orthogonal relation to the first portion of the depressor section.

In certain embodiments, the stop may include a generally U-shaped configuration.

In certain embodiments, the bite block may include a retention structure configured and dimensioned for contact with the patient's teeth to inhibit inadvertent removal of the bite block.

In certain embodiments, the upper member may include a first portion having a generally linear configuration and a second portion having an arcuate configuration.

In certain embodiments, the first portion of the upper member may be connected to, e.g., integrally formed with, the retention structure.

In certain embodiments, the second portions of the upper and lower members may each include a curvature that mimics a contour defined by the patient's tongue.

In certain embodiments, the upper and lower members may be generally planar in configuration.

In certain embodiments, the web may include at least one opening extending transversely through the web.

In certain embodiments, the at least one opening in the web may include a first opening and a second opening. It is envisioned that the first opening may define a first configuration and that the second opening may define a second, different configuration.

In certain embodiments, the depressor section may be dimensioned such that a distalmost end of the depressor section is positionable adjacent a base of the patient's tongue when the airway device is properly oriented in the patient's mouth. For example, in certain embodiments, the depressor section may define a length within the range of approximately 2" to approximately 4".

In another aspect of the present disclosure, an airway device is disclosed that includes a depressor section configured and dimensioned to contact a patient's tongue. The depressor section includes a web, upper and lower members that extend laterally from the web such that the depressor section defines a generally I-shaped transverse cross-sectional configuration, and a stop that depends transversely from the lower member.

In certain embodiments, the lower member may include a first portion having a generally linear configuration and a second portion having an arcuate configuration.

In certain embodiments, the stop may be positioned in generally orthogonal relation to the first portion of the lower member.

In certain embodiments, the stop may include a generally U-shaped configuration.

In certain embodiments, the web may include at least one opening extending transversely therethrough.

In another aspect of the present disclosure, an airway device is disclosed that includes a bite block configured and dimensioned for positioning between a patient's upper and lower teeth, and a depressor section that extends from the bite block. The bite block includes a retention structure that is configured and dimensioned for contact with the patient's teeth to inhibit inadvertent removal of the bite block, and the depressor section includes a web, upper and lower members that extend laterally from the web, and a stop. The upper member includes a generally linear first portion integrally formed with the retention structure of the bite block and an arcuate second portion, and the lower member includes a generally linear first portion and an arcuate second portion. The stop extends from the first portion of the lower member in generally orthogonal relation.

In certain embodiments, the web may include at least one opening extending transversely therethrough.

DETAILED DESCRIPTION

Figure 1:
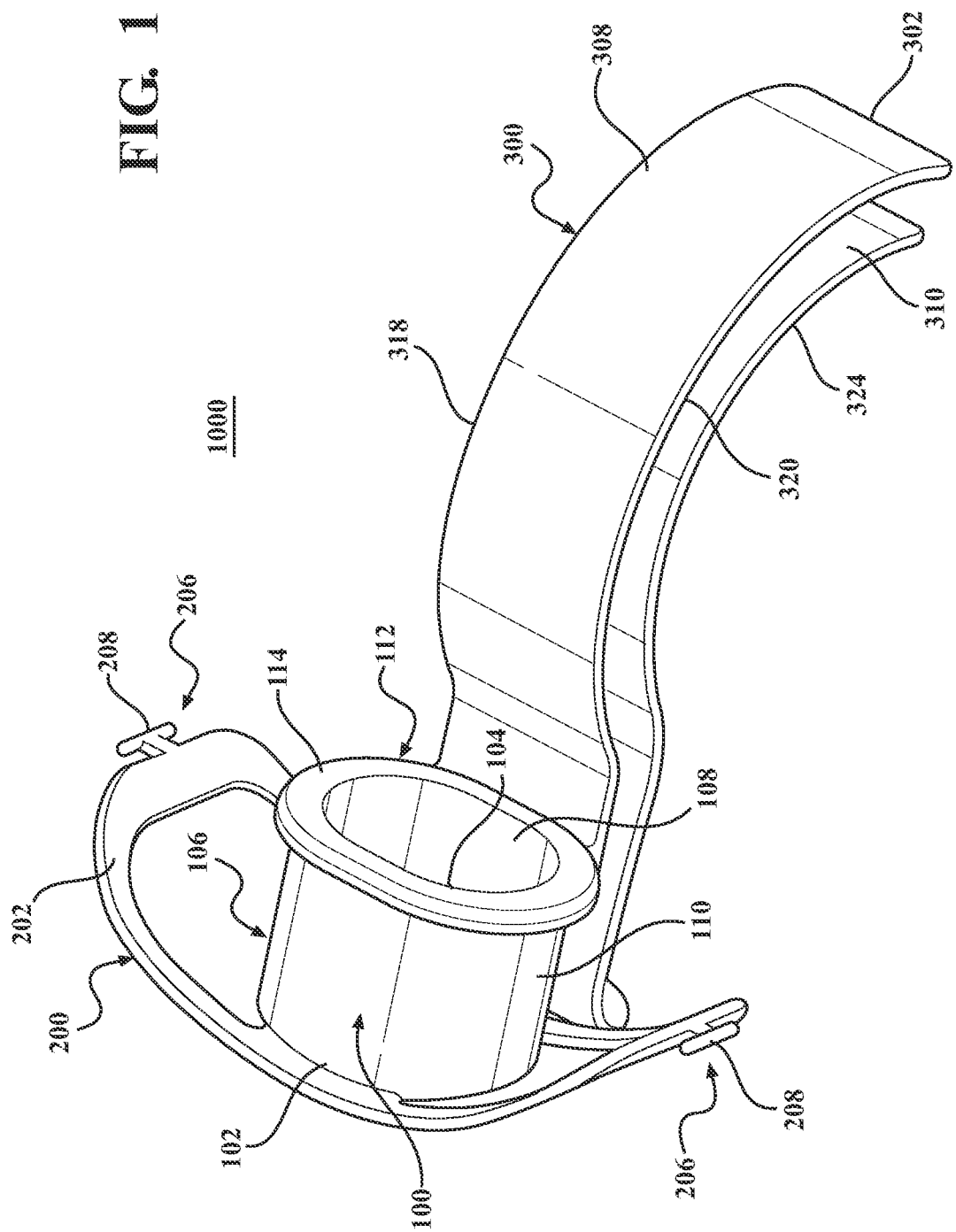
FIG. 1 is a top perspective view of one embodiment of an airway device in accordance with the principles of the present disclosure that includes a bite block, a guard, and a depressor section.

Various embodiments of the present disclosure will now be described in detail with reference to the figures, wherein like referenced numerals identify similar or identical elements. With reference now to FIGS. 1-4, an airway device 1000 utilized during certain medical procedures is illustrated that is configured and dimensioned to: (i) keep a patient's airway open; (ii) facilitate the insertion and removal of medical tools, e.g., endoscopes and endotracheal tubes; and (iii) support and protect the medical tools during insertion and removal, e.g., from damage by the patient's teeth. Throughout the present disclosure, the term "patient" should be understood to refer to a human or animal, and reference to "the patient's tongue" should be understood to refer generally to the inherent anatomy of a human or animal tongue including shape, length, size, etc.

The airway device 1000 defines an overall length L (FIG. 2) in the range of approximately 3" to approximately 5" to facilitate use with a variety of patients and includes a bite block 100, a guard 200, and a depressor section 300. The airway device 1000, and the various components thereof, may be formed from any suitable biocompatible material, such as, for example, plastics or rubbers, either individually or in combination. The airway device 1000 may be manufactured in any suitable manner, such as, for example, via injection molding, extrusion, or 3-D printing. In one particular embodiment, the airway device 100 may be manufactured such that the airway device 1000 is monolithically formed from a single piece of material, whereby the individual components of the airway device 1000, i.e., the bite block 100, the guard 200, and the depressor section 300, are integrally formed.

The bite block 100 is configured and dimensioned for positioning in a patient's mouth. More specifically, the bite block 100 defines a width $W_{BB}$ (FIG. 3), a height $H_{BB}$ (FIG. 3), and a depth $D_{BB}$ (FIG. 2) that permit comfortable positioning of the bite block 100 between the patient's teeth without requiring the patient's mouth to be strained in an open position. For example, the width $W_{BB}$ of the bite block 100 may be within the range of approximately 1" to approximately 1.5", the height $H_{BB}$ of the bite block 100 may be within the range of approximately 0.83" to approximately 1.4", and the depth $D_{BB}$ of the bite block 100 may be within the range of approximately 1" to approximately 1.5".

The bite block 100 includes respective proximal and distal ends 102, 104, and a body 106 defining an access passage 108 that extends through the bite block 100 to permit the insertion and removal of one or more medical tools, e.g., an endoscope (not shown), an endotracheal tube (not shown), etc. Although illustrated as being generally cylindrical and oval in the embodiment shown in FIGS. 1-4, the bite block 100 and the access passage 108 may assume any suitable geometric configuration, e.g., circular, cylindrical, tubular, etc. The body 106 of the bite block 100 includes a wall 110 (FIG. 3) having a thickness T within the range of approximately 0.5" to approximately 1", and the access passage 108 defines an internal dimension O within the range of approximately 0.5" to approximately 1.5".

Figure 3:
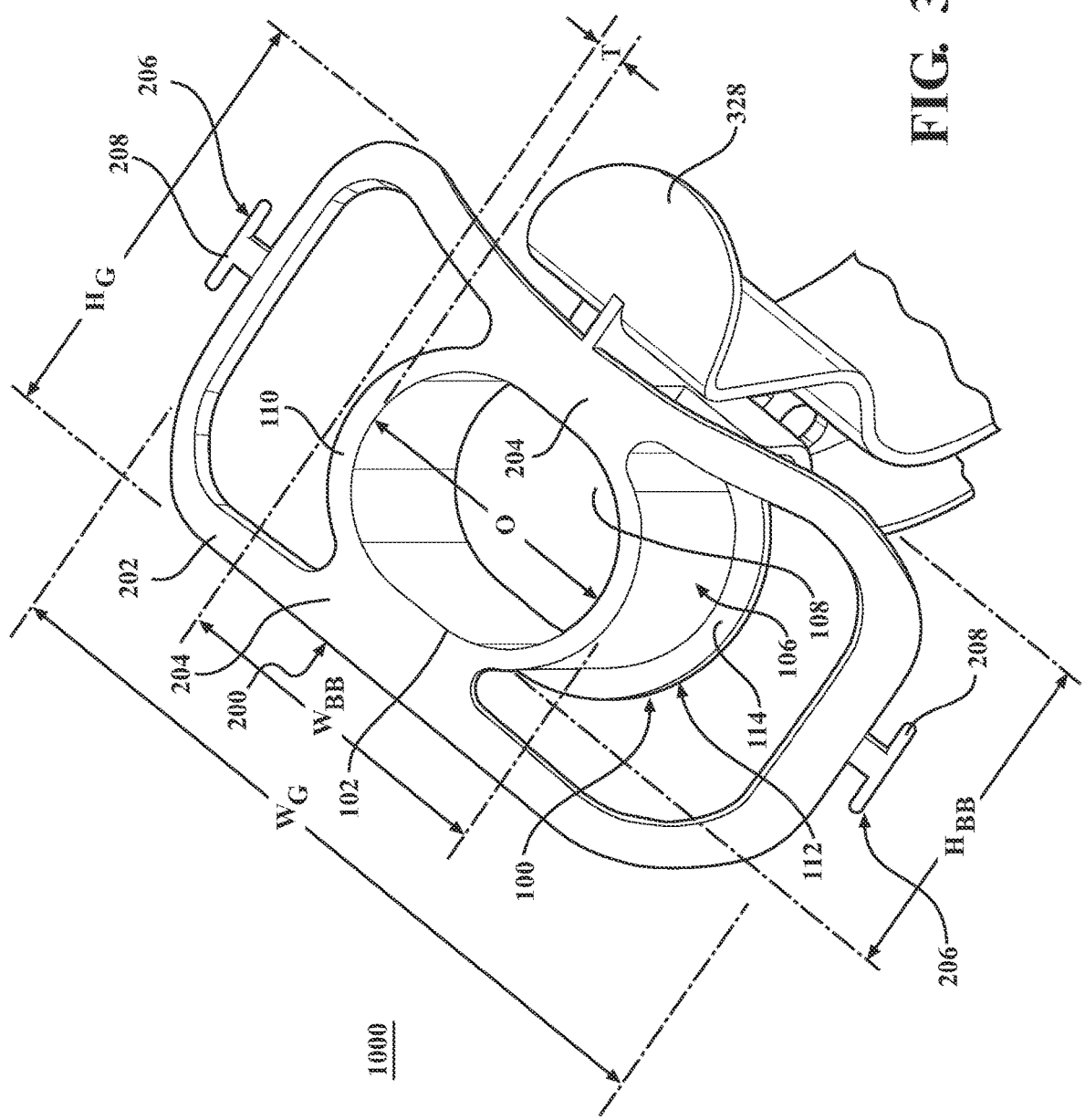
FIG. 3 is a (partial) end perspective view of the airway device shown in FIG. 1.
Figure 4:
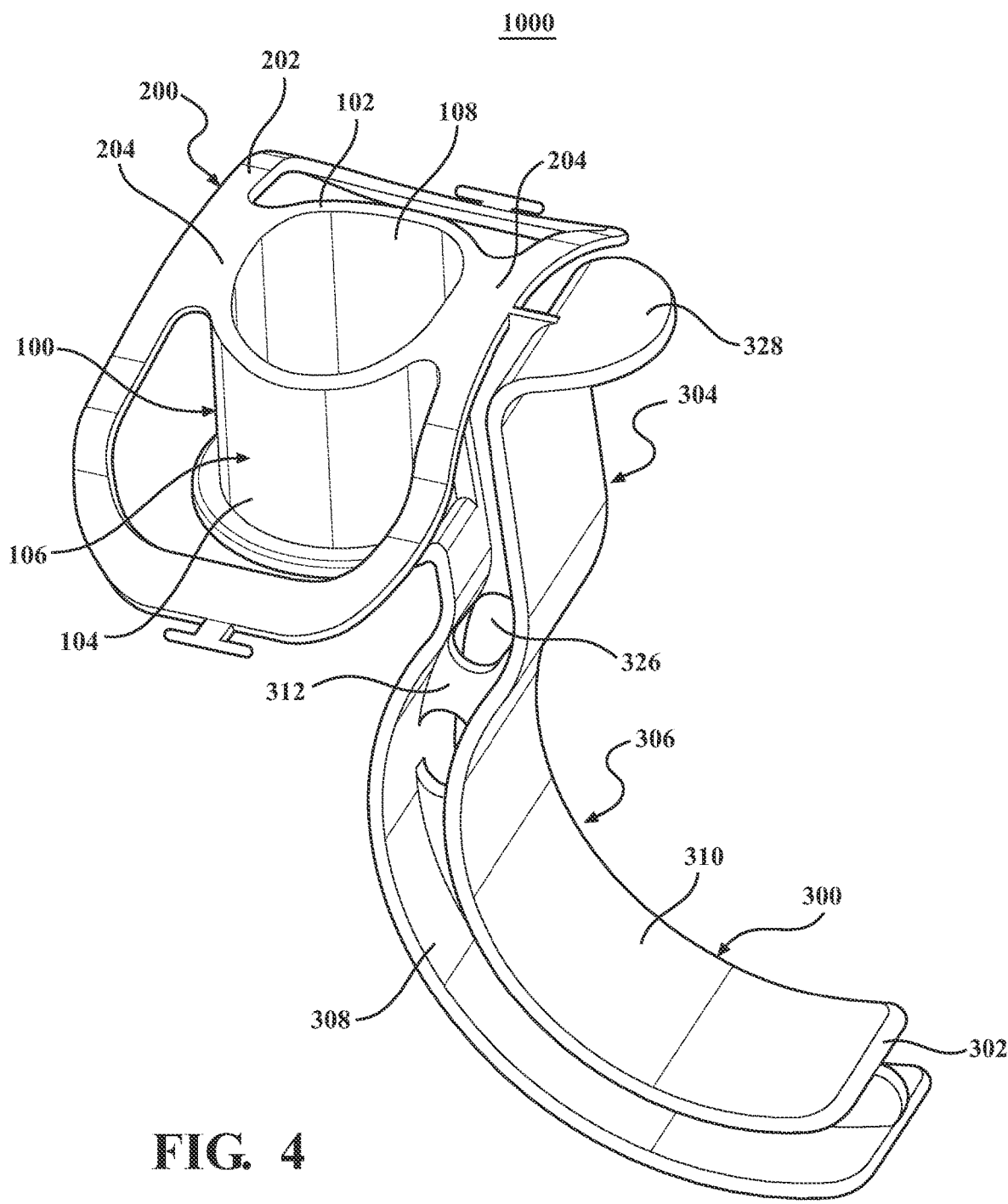
FIG. 4 is a side perspective view of the airway device shown in FIG. 1.
Figure 5:
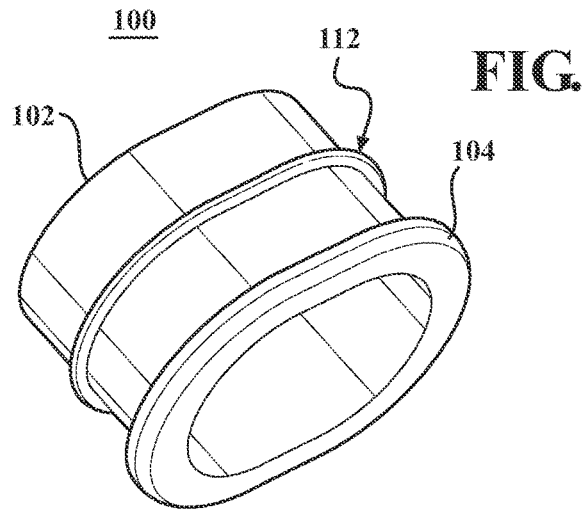
FIG. 5 is a (partial) side view of an alternative embodiment of the bite block seen in FIGS. 1-4.
Figure 6:
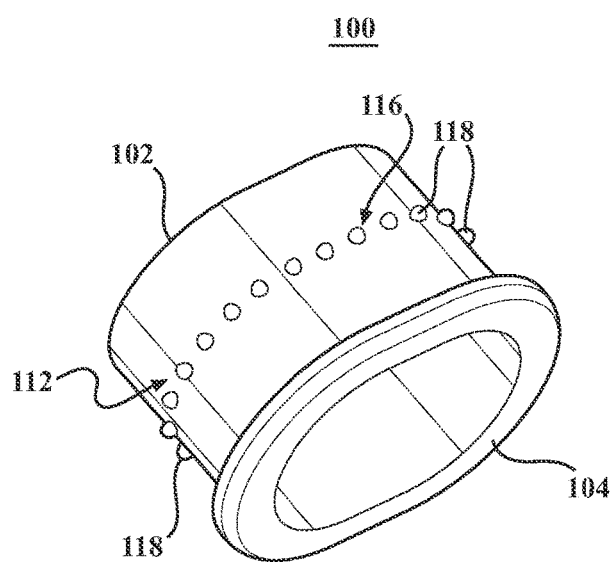
FIG. 6 is a (partial) side view of another alternative embodiment of the bite block seen in FIGS. 1-4.
Figure 7:
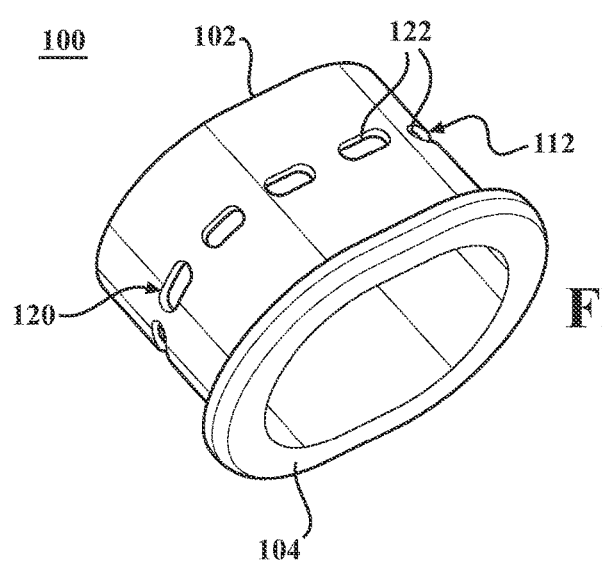
FIG. 7 is a (partial) side view of yet another alternative embodiment of the bite block seen in FIGS. 1-4.
Figure 8:
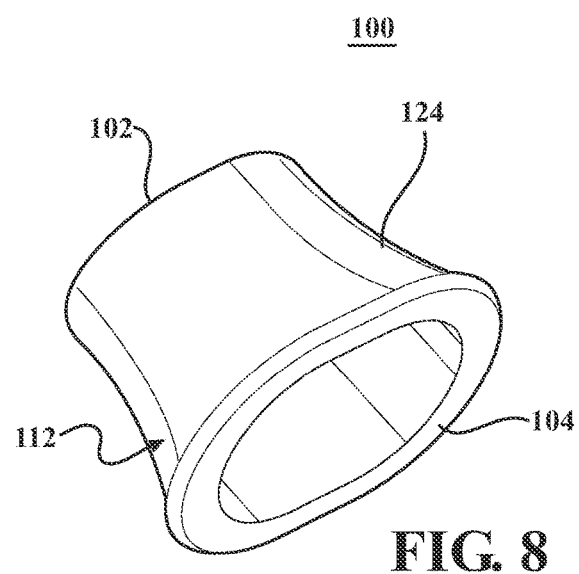
FIG. 8 is a (partial) side view of even another alternative embodiment of the bite block seen in FIGS. 1-4.

As seen in FIGS. 1-4, in certain embodiments, the bite block 100 further includes a retention structure 112 that is configured and dimensioned to inhibit or prevent inadvertent removal of the bite block 100 from the patient's mouth via engagement with the patient's teeth, which may be any structure suitable for this intended purpose. For example, in the particular embodiment illustrated in FIGS. 1-4, the retention structure 112 is depicted as a rib or flange 114 located adjacent to and integral with the distal end 104 of the bite block 100 that circumscribes the bite block 100 and extends radially outward therefrom. It should be appreciated, however, that the location and/or the configuration of the retention structure 112 may be varied in alternate embodiments without departing from the scope of the present disclosure. For example, the retention structure 112 may be positioned between the respective proximal and distal ends 102, 104 of the bite block 100, as seen in FIG. 5, by extending radially outward from the wall 110 of the body 106 of the bite block 100. In another embodiment, the retention structure 112 may include one or more projections 116, e.g., rounded detents 118, as seen in FIG. 6, that extend outward from the wall 110 of the body 106 of the bite block 100. In yet another embodiment, one or more indentations 120, e.g., cavities, channels, or depressions 122, as seen in FIG. 7, may extend in or through the wall 110 of the body 106 of the bite block 100, either individually, or in combination. In even another embodiment, it is envisioned that the retention structure 112 may include a tapered segment 124 of the wall 110 of the body 106 of the bite block 100, as seen in FIG. 8, such that an outer dimension, e.g., diameter, of the bite block 100 increases gradually from the proximal end 102 towards the distal end 104 thereof.

With reference again to FIGS. 1-4, the guard 200 is configured and dimensioned for positioning adjacent the patient's lips and surrounding areas to inhibit or prevent over-insertion of the airway device 1000 into the patient's mouth or airway. The guard 200 is positioned integral with and adjacent to the proximal end 102 of the bite block 100 and extends laterally outward therefrom to define a width $W_G$ (FIG. 3) within the range of approximately 1" to approximately 4." The guard 200 defines a height $H_G$ (FIG. 3) within the range of approximately 1.5" to approximately 2", and includes a flange 202 that is connected to the bite block 100 at bridge portions 204 located in the center of the guard 200. The bridge portions 204 serve to connect the flange 202 to the bite block 100, and permit a certain amount of relative movement between the flange 202 and the bite block 100 to create flexibility in positioning the flange 202 to the patient's mouth in order to increase patient comfort.

In the embodiment illustrated in FIGS. 1-4, the flange 202 includes a substantially arcuate configuration, in which the flange 202 has a substantially rectangular, hollow configuration that curves towards the distal end 104 of the bite block 100 such that a space is provided between the flange 202 and the bite block 100 except for where the flange 202 is connected to the bite block 100 via the bridge portions 204. For example, the flange 202 may define a radius of curvature within the range of approximately 1" to approximately 2". Alternatively, it is envisioned that the flange 202 may be devoid of any such deliberate curvature, and thus, generally planar in configuration.

The guard 200 may further include connectors 206, as seen in FIGS. 1-4, to facilitate the connection of supports to the airway device 1000. For example, the guard 200 may include T-shaped projections 208 positioned adjacent the lateral ends of the guard 200 that are configured and dimensioned for connection to straps (not shown) such that the straps can extend around the patient's head, e.g., to further support the airway device 1000 and assist in inhibiting or preventing over-insertion of the airway device 1000 into the patient's mouth or airway.

With continued reference to FIGS. 1-4, the depressor section 300 extends distally from the bite block 100 and is configured and dimensioned for contact with the patient's tongue and other soft tissues of the patient's mouth. More specifically, the depressor section 300 is configured and dimensioned to press the patient's tongue towards the floor of the patient's mouth and maintain the position of the patient's tongue to guard against obstruction of the patient's airway and/or apnea. To facilitate proper depression, in one embodiment, the depressor section 300 defines a length $L_D$ (FIG. 2) within the range of approximately 2" to approximately 4" such that a distalmost end 302 (FIGS. 1, 2) of the depressor section 300 is positionable adjacent a base of the patient's tongue when the airway device 1000 is properly oriented in the patient's mouth.

The depressor section 300 includes a first portion 304 (FIG. 2) that is connected to or integral with the bite block 100 and a second portion 306 that extends distally from the first portion 304. In the embodiment illustrated in FIGS. 1-4, for example, the first portion 304 includes a generally planar configuration, and the second portion 306 includes a generally arcuate configuration that mimics the contour of the patient's tongue and portion of the throat, e.g., such that the second portion defines a radius of curvature within the range of approximately 0.2" to approximately 0.5".

The depressor section 300 includes respective upper and lower members 308, 310 that are substantially parallel and connected to and separated by a web 312. The upper and lower members 308, 310 extend along both the planar first portion 304 and the arcuate second portion 306 of the depressor section 300. The first portion 304 of the upper member 308 is connected to or integral with a portion of the rib 114 formed on the bite block 100 and extends away from the bite block 100 to the arcuate second portion 306. The planar first portion 304 of the lower member 310 extends along the length of the bite block 100 and is connected to the bite block 100 and a portion of the guard 200 by the web 312 which may be connected to or integrally formed with the planar first portion 304 of the lower member 310, the bite block 100, and the guard 200.

Figure 9:
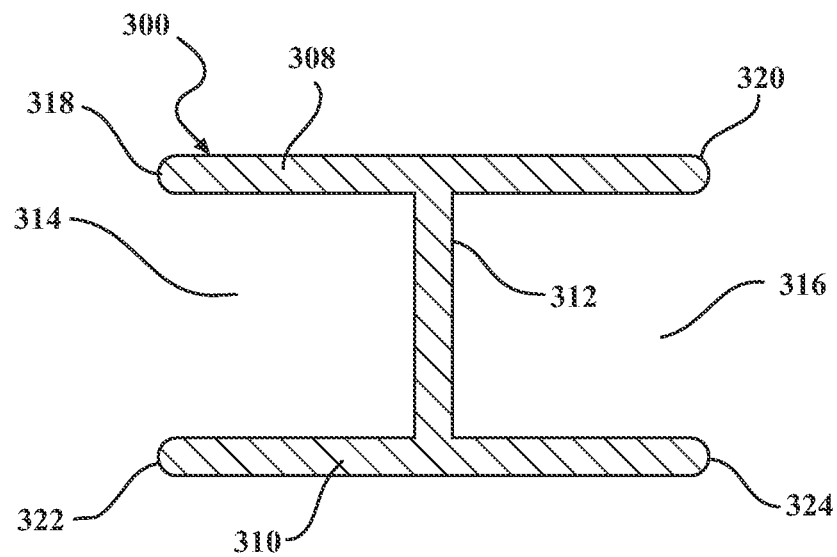
FIG. 9 is a transverse cross-sectional view of the depressor section taken along line 8-8 in FIG. 2.

As can be appreciated through reference to FIG. 9, for example, as the depressor section 300 extends into the arcuate second portion 306, the upper and lower members 308, 310 extend laterally outward from the web 312 such that the depressor section 300 includes a generally I-shaped transverse cross-sectional configuration wherein the web 312 is substantially perpendicular to the upper and lower members 308, 310 of the depressor section 300. The I-shaped transverse cross-sectional configuration defines lateral channels 314, 316 configured and dimensioned to accommodate one or more medical tools, e.g., a suction tube or an airway tube, that are positioned on opposite sides of the web 312.

Figure 10:
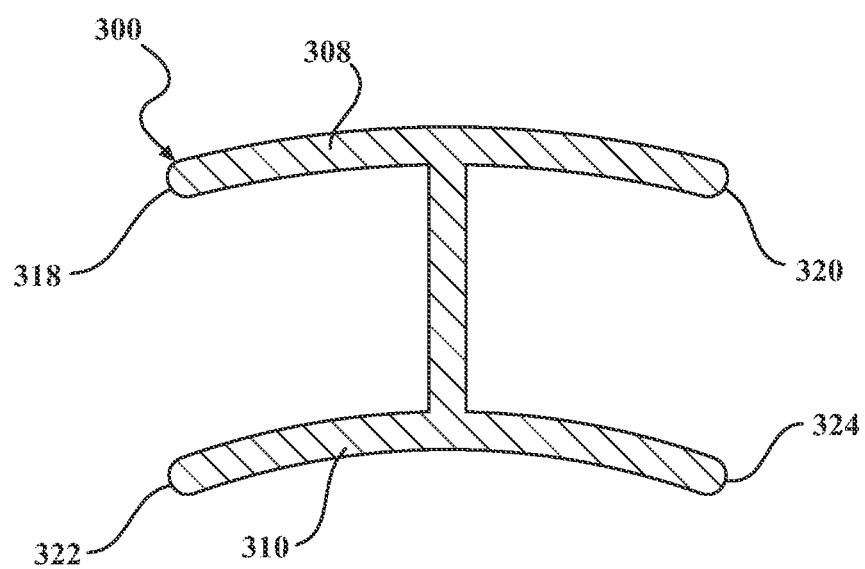
FIG. 10 is a transverse cross-sectional view of an alternate embodiment of the depressor section.

As seen in FIGS. 1 and 9, the upper member 308 includes lateral ends 318, 320, and the lower member 310 includes lateral ends 322, 324. While each of the members 308, 310 is illustrated as being generally planar in configuration in the embodiment illustrated in FIGS. 1 and 9, in alternate embodiments, either or both of the members 308, 310 may include a curvate configuration, as seen in FIG. 10.

Figure 2:
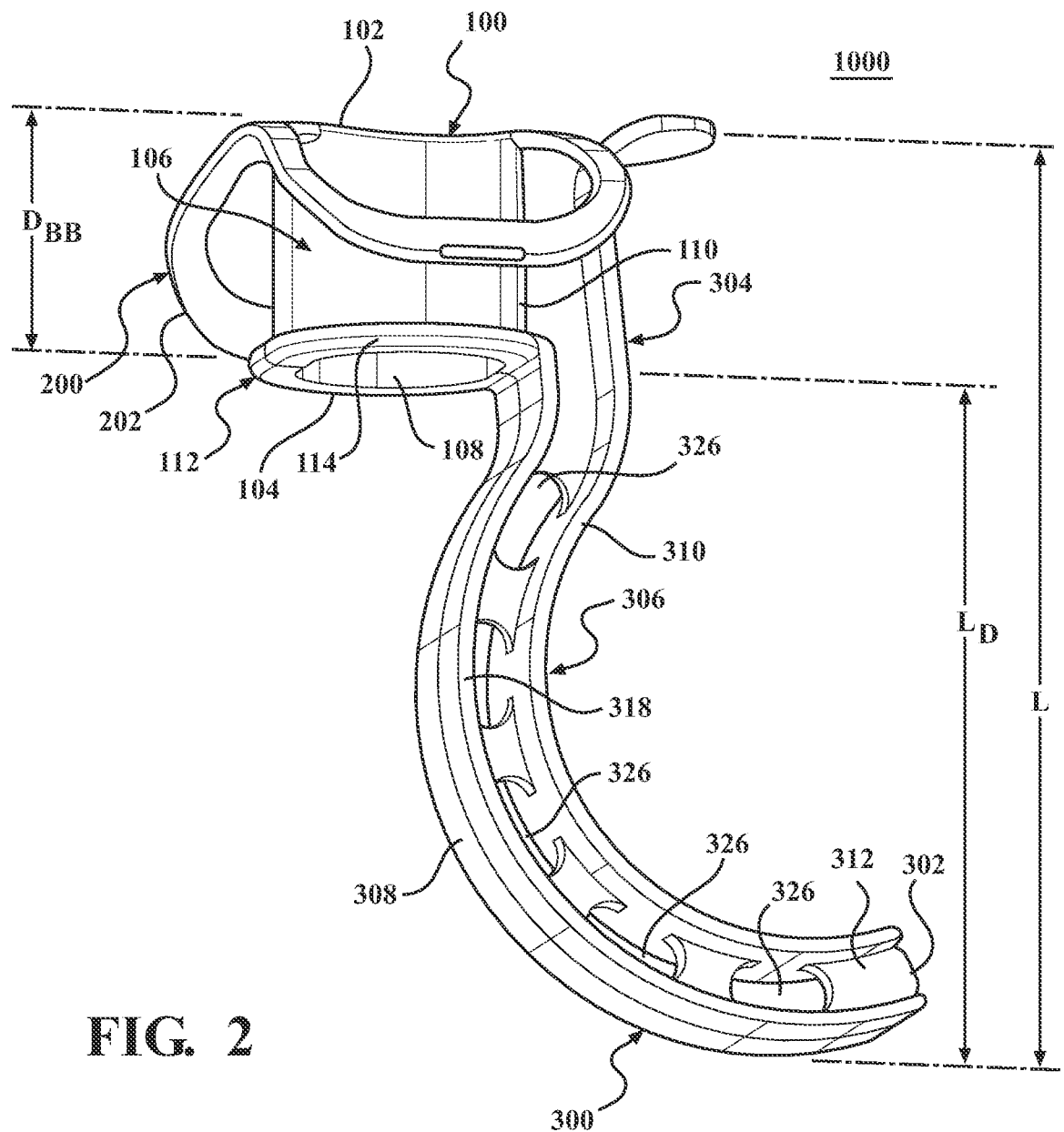
FIG. 2 is a side perspective view of the airway device shown in FIG. 1.
Figure 11:
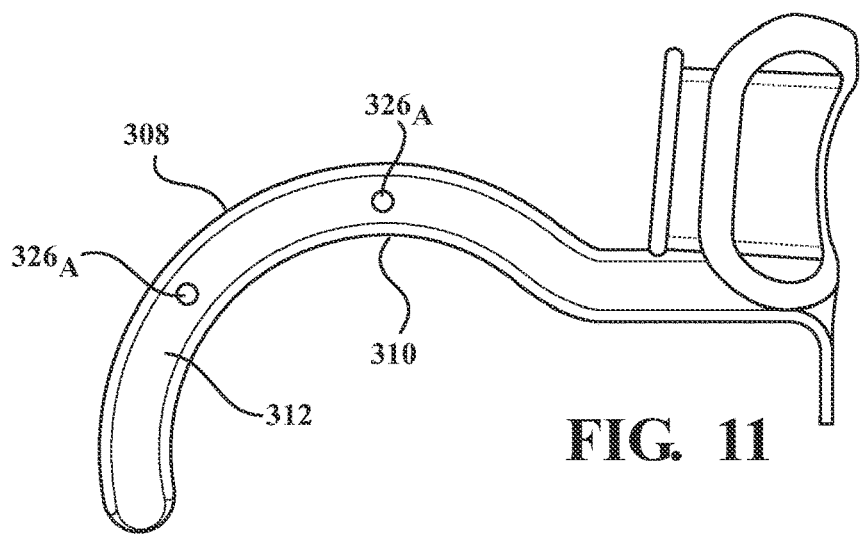
FIG. 11 is a side view of an alternate embodiment of the airway device shown in FIG. 1.
Figure 12:
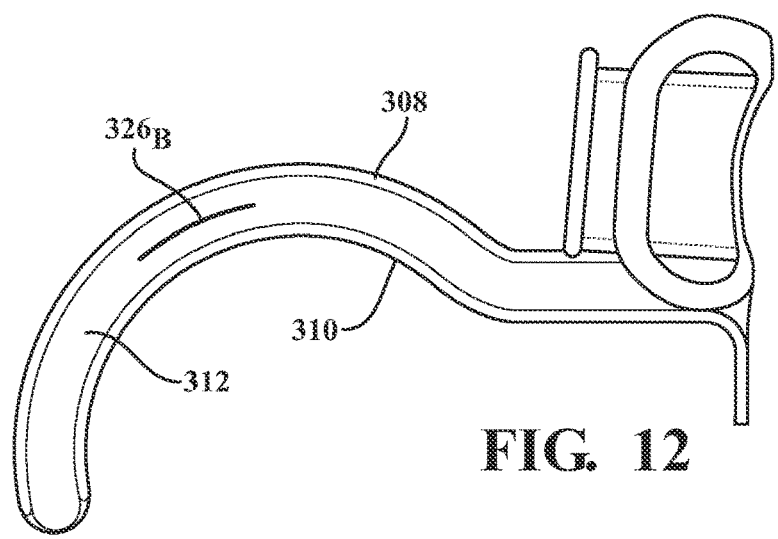
FIG. 12 is a side view of another alternative embodiment of the airway device shown in FIG. 1.
Figure 13:
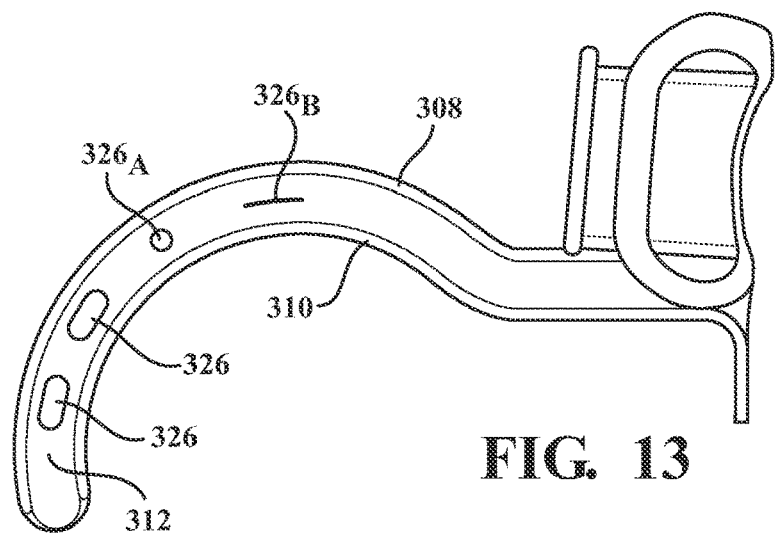
FIG. 13 is a side view of yet another alternative embodiment of the airway device shown in FIG. 1.

The web 312 separating the members 308, 310 includes one or more openings 326 (FIG. 2). The openings 326 may be formed during manufacture, e.g., during an injection molding process, and may be configured and dimensioned to receive medical tools, such as suctions tubes (not shown), airway tubes (not shown), or the like. The openings 326 extend through the web 312 such that an inserted medical tool will extend transversely through the depressor section 300, i.e., in a direction transverse in relation to the length $L_D$ (FIG. 2) of the depressor section 300. Although shown as including five openings 326 that are each generally elliptical in configuration, in alternate embodiments, the number and/or configuration of the openings 326 may be altered or varied. For example, as seen in FIG. 11, the web 312 may include a pair of openings $326_A$ that are generally circular in configuration. In FIG. 12, a single opening $326_B$ is provided and configured as a slit. In FIG. 13, a combination of openings 326 that vary in configuration may be utilized, such as a pair of elliptical openings 326, a single circular opening $326_A$, and a single opening $326_B$ configured as a slit.

To further inhibit or prevent against over-insertion of the airway device 1000 into the patient's mouth or airway, in certain embodiments, the depressor section 300 may include a stop 328 (FIGS. 3, 4), for example, to prevent over insertion of the airway device 1000 and/or further stabilize the oral airway device 1000 in the patient's mouth. The stop 328 extends transversely in relation to the lower member 310. More specifically, in the illustrated embodiment, the stop 328 extends downwardly, i.e., towards the patients' bottom teeth, from an end of the planar first portion 304 of the lower member 310 and bends away from the bite block 100 such that the stop 328 is positioned in generally orthogonal relation to the lower member 310. As seen in FIG. 2-4, for example, the stop 328 may be integrally formed with the end of the planar first portion 304 of the lower member 310 and may be generally U-shaped or curved in configuration, e.g., so as not to harm the patient's mouth. Although illustrated as being a component of the depressor section 300 in the embodiment illustrated in FIGS. 1-4, in alternate embodiments, the location of the stop 328 may be varied. For example, the stop 328 may extend downwardly from the bite block 100 or the guard 200.

With reference now to FIGS. 1-4, use of the airway device 1000 will be discussed in connection with a medical procedure, such as an EGD procedure or an ERCP (endoscopic retrograde cholangiopancreatography) procedure. To ensure that a patient receives sufficient oxygen, e.g., while unconscious under general anesthesia, the airway device 1000 is placed in the patient's mouth such that the bite block 100 is positioned between the patient's upper and lower teeth. After placement, the general position of the airway device 1000 is maintained via engagement of the patient's teeth with the bite block 100, and engagement of the guard 200 with the patient's lips and/or the surrounding areas. When properly positioned within the patient's mouth, the depressor section 300 extends above and behind the patient's tongue so as to press the patient's tongue against the floor of the patient's mouth. The curved configuration of the second portion 306 (FIG. 2) of the depressor section 300 "cups" the patient's tongue, with the distalmost end 302 of the depressor section 300 being positioned at or adjacent the base of the patient's tongue so as to apply a force directed forwards, i.e., towards the patient's teeth, in order to urge the patient's tongue away from the patient's posterior pharynx, and prevent the patient's tongue from falling backwards into the patient's airway.

After placement of the airway device 1000, medical tools, e.g., endoscopes or ventilation tubes, may be inserted through the access passage 108 extending through the bite block 100, and into the patient's oral cavity, esophagus, airway, stomach, and/or duodenum. The bite block 100 will function to maintain the medical tool(s) in the correct position(s), and will protect the medical tool(s) from damage, e.g., from the patient's teeth. Additionally, or alternatively, medical tools can be inserted into, and positioned within, the openings 326 formed in the web 312 of the depressor section 300, and/or the lateral channels 314, 316 (FIG. 9) flanking the web 312, if necessary or desirable.

Persons skilled in the art will understand that the various embodiments of the disclosure described herein, and shown in the accompanying figures, constitute non-limiting examples, and that additional components and features may be added to any of the embodiments discussed herein above without departing from the scope of the present disclosure. Additionally, persons skilled in the art will understand that the elements and features shown or described in connection with one embodiment may be combined with those of another embodiment without departing from the scope of the present disclosure, and will appreciate further features and advantages of the presently disclosed subject matter based on the description provided. Variations, combinations, and/or modifications to any of the embodiments and/or features of the embodiments described herein within the abilities of a person having ordinary skill in the art are also within the scope of the disclosure, as are alternative embodiments that may result from combining, integrating, and/or omitting features from any of the disclosed embodiments.

Where numerical ranges or limitations are expressly stated, such express ranges or limitations should be understood to include iterative ranges or limitations of like magnitude falling within the expressly stated ranges or limitations, e.g., from about 1 to about 10 includes 2, 3, 4, etc., and greater than 0.10 includes 0.11, 0.12, 0.13, etc. Additionally, whenever a numerical range with a lower limit, $L_L$, and an upper limit, $L_u$, is disclosed, any number falling within the range is specifically disclosed. In particular, the following numbers within the range are specifically disclosed: $L=L_L+k*(L_U-L_L)$, wherein k is a variable ranging from 1 percent to 100 percent with a 1 percent increment, i.e., k is 1 percent, 2 percent, 3 percent, 4 percent, 5 percent, 50 percent, 51 percent, 52 percent, . . . , 95 percent, 96 percent, 97 percent, 98 percent, 99 percent, or 100 percent. Moreover, any numerical range defined by two L numbers, in accordance with the above discussion, is also specifically disclosed.

Use of the term "optionally" with respect to any element of a claim means that the element may be included or omitted, both alternatives being within the scope of the claim. Additionally, use of broader terms such as "comprises," "includes," and "having" should be understood to provide support for narrower terms such as "consisting of," "consisting essentially of," and "comprised substantially of." Accordingly, the scope of protection is not limited by the description set out above, but is defined by the claims that follow, and includes all equivalents of the subject matter of the claims.

In the preceding description, reference may be made to the spatial relationship between the various structures illustrated in the accompanying drawings, and to the spatial orientation of the structures. However, as will be recognized by those skilled in the art after a complete reading of this disclosure, the structures described herein may be positioned and oriented in any manner suitable for their intended purpose. Thus, the use of terms such as "above," "below," "upper," "lower," "inner," "outer," etc., should be understood to describe a relative relationship between structures, and/or a spatial orientation of the structures.

Additionally, terms such as "approximately" and "generally" should be understood to allow for variations in any numerical range or concept with which they are associated. For example, it is envisioned that the use of terms such as "approximately" and "generally" should be understood to encompass variations on the order of 25%, or to allow for manufacturing tolerances and/or deviations in design.

Each and every claim is incorporated as further disclosure into the specification, and represent embodiments of the present disclosure. Also, the phrases "at least one of A, B, and C" and "A and/or B and/or C" should each be interpreted to include only A, only B, only C, or any combination of A, B, and C.

The invention claimed is:

1. An airway device, comprising:
   a bite block having a proximal end and a distal end configured for positioning between a patient's teeth, the bite block defining an access passage configured to receive a medical tool; and
   a depressor section having a first planar section connected to a lower end of the bite block and a second arcuate portion extending from the first planar section such that the first planar section of the depressor section is spaced vertically from the access passage along a first axis.

2. The airway device of claim 1, wherein the bite block and the depressor section are integrally formed from a single piece of material.

3. The airway device of claim 1, wherein the bite block includes a generally cylindrical configuration.

4. The airway device of claim 3, wherein the access passage includes a generally elliptical cross-sectional configuration.

5. The airway device of claim 2, wherein the bite block includes a retention structure that circumscribes and is integral with the distal end of the bite block for contact with the patient's teeth to inhibit inadvertent removal of the bite block.

6. The airway device of claim 5, wherein the bite block includes a tapered configuration narrowing from the distal end to the proximal end.

7. The airway device of claim 5, wherein the retention structure extends laterally outward from the distal end of the bite block.

8. The airway device of claim 5, wherein the retention structure extends inwardly into the bite block.

9. The airway device of claim 1, further including a guard extending laterally outward from the bite block along a second axis transverse in relation to the first axis.

10. The airway device of claim 9, wherein the guard includes a flange and a bridge portion connecting the flange to the bite block such that the guard defines a first open interior region on a first lateral side of the bite block and a second open interior region on a second lateral side of the bite block to increase flexibility of the guard and patient comfort.

11. The airway device of claim 10, wherein the guard further includes at least one connector configured for engagement with a wearable support.

12. The airway device of claim 11, wherein the at least one connector includes a first connector at a first lateral end of the flange and a second connector at a second lateral end of the flange.

13. The airway device of claim 1, further including a stop extending transversely from the depressor section and adjacent and vertically spaced from the bite block.

14. An airway device, comprising:
a bite block configured for positioning between a patient's teeth, the bite block defining an access passage configured to receive a medical tool;
a depressor section having a first planar section connected to a lower end of the bite block and a second arcuate portion extending from the first planar section such that the depressor section is spaced vertically from the access passage along a first axis;
a stop extending transversely from the depressor section and adjacent the bite block;
wherein the stop includes a generally U-shaped configuration.

15. An airway device, comprising:
a bite block having a cylindrical and oval configuration with an access passage extending therethrough; and
a depressor section having an arcuate portion and a planar portion vertically spaced and extending from the bite block such that the access passage and the depressor section are misaligned.

16. The airway device of claim 15, wherein the bite block and the depressor section are integrally formed from a single piece of material.

17. The airway device of claim 15, further including a guard extending laterally outward from the bite block, the guard defining an open interior region.

18. An airway device, comprising:
a bite block having a cylindrical and oval configuration having an access passage extending therethrough along a first axis;
a retention structure circumscribing a distal end of the bite block;
a depressor section having an arcuate portion and a planar portion extending from and connected to the bite block such that the access passage and the planar portion of the depressor section are spaced apart along a second axis transverse in relation to the first axis; and
a guard extending outwardly from the bite block along a third axis transverse in relation to the first axis and the second axis.

19. The airway device of claim 18, wherein the bite block and the depressor section are integrally formed from a single piece of material.

20. The airway device of claim 18, wherein the guard defines an open interior region.

* * * * *